United States Patent [19]

Cleeland, Jr. et al.

[11] 3,969,373
[45] July 13, 1976

[54] FLUOROGENIC 2-OXY-3(2H)-FURANONE MATERIALS

[75] Inventors: Roy Cleeland, Jr., Short Hills; Emanuel Grunberg, North Caldwell; Willy Leimgruber, Montclair; Manfred Weigele, North Caldwell, all of N.J.

[73] Assignee: Hoffmann-La Roche Inc., Nutley, N.J.

[22] Filed: June 26, 1975

[21] Appl. No.: 590,655

Related U.S. Application Data

[63] Continuation-in-part of Ser. No. 338,019, March 5, 1973, abandoned.

[52] U.S. Cl. .................. 260/347.3; 260/326.16; 260/347.8; 260/348 R; 260/570.5 R; 260/592; 252/301.31; 252/301.32; 424/7
[51] Int. Cl.² ........................... C07D 307/60
[58] Field of Search ........... 260/347.8, 347.4, 347.5, 260/326.16, 347.3

[56] References Cited
OTHER PUBLICATIONS

Weigele et al., J. Am. Chem. Soc., vol. 94, pp. 5927–5928, (1972).

Primary Examiner—Harry I. Moatz
Attorney, Agent, or Firm—Samuel L. Welt; George M. Gould; Raymond R. Wittekind

[57] ABSTRACT

Compounds of the formula

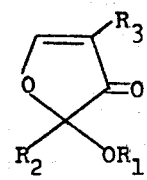

I wherein $R_1$ is lower alkyl or phenyl lower alkyl; $R_2$ is phenyl or substituted phenyl; and $R_3$ is substituted or unsubstituted phenyl, naphthyl or indolyl; are fluorogenic reagents which react with primary amino groups to form fluorophors. The above compounds are useful for fluorescent labeling of materials of biological importance.

9 Claims, No Drawings

FLUOROGENIC 2-OXY-3(2H)-FURANONE MATERIALS

This application is a continuation-in-part of prior U.S. patent application Ser. No. 338,019, filed Mar. 5, 1973, now abandoned.

BACKGROUND OF THE INVENTION

The rapid identification of microorganisms and other pathogenic antigens with the help of fluorescent antibodies is a most important example of the diagnostic utility of fluorophorbic protein conjugates. Existing procedures for fluorescent labeling of proteins, for example, labeling with fluorescein isothiocyanate (FITC) rely upon fluorophors with reactive functionalities which will covalently bind to proteins. However, this methodology is encumbered by serious disadvantages, stemming mainly from the need for extensive purification to remove any excess reagent which would otherwise non-specifically interfere in immunoassays.

It would thus be desirable to have a material for labeling which itself is non-fluorescent but which reacts with the materials to be labeled to produce fluorescent conjugates thus avoiding tedious purification.

BRIEF DESCRIPTION OF THE INVENTION

The present invention relates to a novel series of compounds represented by the formula

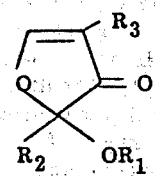

I wherein $R_1$ is lower alkyl, phenyl lower alkyl; $R_2$ is phenyl or substituted phenyl; and $R_3$ is substituted or unsubstituted phenyl, naphthyl or indolyl.

These compounds of themselves are non-fluorescent but produce highly fluorescent substances upon reaction with primary amine-containing compounds and are therefore designated as "fluorogens". These compounds are particularly useful for the fluorescent labeling of materials of biological importance, a detailed discussion of which technique will be presented below.

In the specification and the appended claims, the term "lower alkyl" shall mean a monovalent, saturated, straight or branched chain hydrocarbon substituent containing up to and including 8 carbon atoms. Examples of lower alkyl groups are methyl, ethyl, n-propyl, n-butyl, hexyl, octyl, isopropyl, tert-butyl, and so forth. The term "phenyl lower alkyl" refers to a lower alkyl group as defined above which is attached to a phenyl ring, for example, benzyl, phenylethyl, phenylpropyl, and so forth. The term "substituted" as applied to phenyl, naphthyl or indolyl refers to these groups substituted with one or more of the following substituents: halogen (i.e., fluorine, chlorine, bromine or iodine), lower alkyl, trifluoromethyl, lower alkoxy, nitro, cyano, carboxy and carboxy lower alkyl. The term "carboxy lower alkyl" refers to a lower alkyl group as defined above which is attached to a carboxy group. The term "lower alkoxy" shall mean a group having a lower alkyl residue linked to an ether oxygen and having its valence bond from the ether oxygen. Examples of lower alkoxy groups are methoxy, ethoxy, n-propoxy, n-butoxy, isopropoxy, tert-butoxy, and so forth.

Preferred compounds of formula I are those wherein $R_1$ is lower alkyl, $R_2$ is phenyl and $R_3$ is phenyl or phenyl substituted by carboxy or carboxy lower alkyl. Particularly preferred compounds of formula I are the compounds wherein $R_1$ is methyl and $R_2$ and $R_3$ are phenyl, i.e., 2-methoxy-2,4-diphenyl-3(2H)furanone, $R_1$ is methyl, $R_2$ is phenyl and $R_3$ is 4-carboxyphenyl, i.e., 2-methoxy-2-phenyl-4-(4-carboxyphenyl)-3(2H)furanone and $R_1$ is methyl, $R_2$ is phenyl and $R_3$ is 4-(2-carboxyethyl)phenyl, i.e., 2-methoxy-2-phenyl-4-[4-(2-carboxyethyl)phenyl]-3(2H)furanone.

Compounds of formula I may be prepared by a multi-step synthetic sequence starting from readily available starting materials of formula II

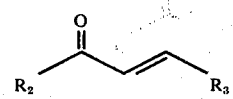

II wherein $R_2$ and $R_3$ are as above.

Compounds of formula II wherein $R_2$ and $R_3$ are phenyl or substituted phenyl are generally referred to as benzalacetophenones or substituted benzalacetophenones.

In the first step, the starting material of formula II is epoxidized under basic conditions to afford an epoxy ketone of formula III

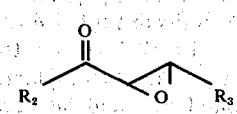

III wherein $R_2$ and $R_3$ are as above.

The epoxidation reaction is carried out by treating a compound of formula II with an excess of hydrogen peroxide in the presence of a strong base. Suitable strong bases for the present reaction include alkali metal hydroxides, e.g., sodium hydroxide and potassium hydroxide; and alkali metal carbonates, e.g., sodium carbonate and potassium carbonate. Suitable solvents for the epoxidation reaction are alcohols, particularly methanol and ethanol, and aqueous alcohol mixtures. The reaction is generally performed at temperatures from about 10° to about 40°C., most preferably from about 20° to about 30°C.

In the next step, the compound of formula III is treated with a strong anhydrous base to cleave the epoxide ring and afford a diketone of formula IV

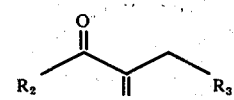

IV wherein $R_2$ and $R_3$ are as above.

Suitable strong anhydrous bases for this cleavage reaction include alkali metal alkoxides such as sodium methoxide, sodium ethoxide, sodium isopropoxide, potassium tert-butoxide, and so forth. As suitable solvents for the cleavage reaction, there may be mentioned anhydrous alcohols, for example, methanol, ethanol, isopropanol and tert-butanol. It is generally preferred to utilize the same alcohol from which the alkoxide base is derived; however, this is not critical, and if a different alcohol is used as solvent, there will be an exchange between the alcohol solvent and the alcohol portion of the alkali metal alkoxide. The cleavage reaction is generally carried out at an elevated temperature, preferably between about 40° and about 100°C., most preferably at the boiling point of the reaction medium.

In the next step, diketone of formula IV is converted to an enamine of formula V

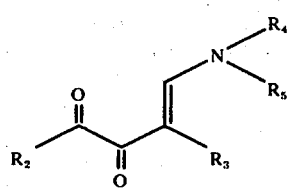

V wherein $R_2$ and $R_3$ are as above, and $R_4$ and $R_5$ taken independently are each lower alkyl and taken together with the nitrogen atom form a 5- or 6-membered heterocyclic ring having at the most one additional heteroatom selected from the group consisting of nitrogen and oxygen.

In this reacton, the diketone of formula IV is reacted with an amino-methenylating agent to afford the enamine.

Suitable amino methenylating agents include lower alkyl acetals of an N,N-disubstituted formamide, e.g., dimethyl formamide dimethyl acetal; tris(secondary amino)methanes, e.g., tris(dimethylamino)methane and tris(piperidino)methane; and bis(secondary amino)lower alkoxy methanes, e.g., bis(dimethyl amino) t-butoxy methane.

The amino moiety

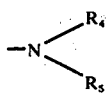

as shown in the structural formula for compound V is introduced from the aminomethenylating agent. Acetals of N,N-disubstituted formamides have the general formula

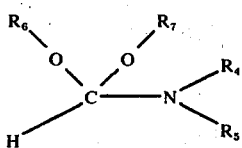

wherein $R_6$ and $R_7$ are each lower alkyl; tris(secondary amino)methanes have the general formula

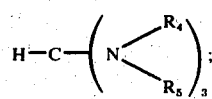

and bis(secondary amino)lower alkoxymethanes have the general formula

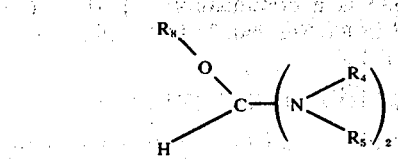

wherein $R_8$ is lower alkyl.
Examples of amino moieties

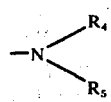

include those where $R_4$ and $R_5$ each taken independently are lower alkyl, e.g., dimethylamino and diethylamino, and those where $R_4$ and $R_5$ taken together with the nitrogen form a 5- or 6-membered heterocyclic ring, e.g., piperidino, morpholino, pyrrolidino, piperazino, imidazolidino, pyrazolidino, and so forth. Examples of lower alkoxy moieties $OR_6$ and $OR_7$ are methoxy, ethoxy, propoxy, n-butoxy, and so forth. Examples of lower alkoxy moieties $OR_8$ are methoxy, ethoxy, tert-butoxy, and so forth.

This reaction may be carried out in any inert organic solvent. Preferred solvents include formamides, especially dimethylformamide. An excess of aminomethenylating agent may also be utilized as solvent.

The preparation of the enamine may be effectuated over a temperature range of from about 0° to about 100° C. although a temperature range from about 10°to about 40° C. is preferred. A temperature of about room temperature is especially preferred.

In the next step, the enamine of formula V is converted to the hydroxy furanone of formula VI

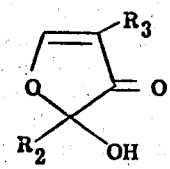

VI

Wherein $R_3$ and $R_4$ are as above.
This conversion involves a basic aqueous hydrolysis. Suitable bases for this hydrolysis include alkali metal hydroxides, e.g., sodium hydroxide and potassium hydroxide; and alkali metal carbonates, e.g., sodium carbonate and potassium carbonate. Suitable temperatures for carrying out the above reaction are from about 0° to about 40° C., most preferably about room temperature. After the hydrolysis is complete, the basic solution is acidified to afford the hydroxy furanone of formula VI.

The hydroxy furanone of formula VI may be then converted to the furanone of formula I by reaction with the appropriate alcohol, either a lower alkanol or aryl lower alkanol, such as methanol, ethanol, benzyl alcohol, phenylethyl alcohol, and so forth. As solvents for this reaction, there may be employed the alcohol itself or a mixture of the alcohol and an inert organic solvent.

It is most preferable to carry out this reaction neat in the desired alcohol. The reaction may suitably be carried out at temperatures from about room temperature to about the boiling point of the solvent medium. It is most preferable to carry out the reaction at a temperature between about 40° and about 80°C.

Compounds of formula I may be interconverted, i.e., the alkoxy group $OR_1$ can be changed, by reaction to the compound of formula I with a suitable lower alkanol or phenyl lower alkanol. Thus, for example, the compound of formula I, wherein $R_1$ is methyl, can be converted to the corresponding compound wherein $R_1$ is benzyl by heating the former compound with a excess of benzyl alcohol.

4-(2-Carboxyelthyl)benzaldehyde, the aldehyde component of the synthesis of 4-(2-carboxyethyl)benzalacetophenone and 4-(2-carboxyethyl)benzal-substituted-acetophenones, is prepared by condensation of terephthalaldehyde with malonic acid in ethanol-pyridine to 4-formylcinnamic acid followed by formation of the dimethylacetal by means of methanolic trimethyl orthoformate, catalytic hydrogenation of the side-chain unsaturation in the presence of 5% palladium-on-carbon suspended in dioxane and hydrolysis of the acetal with dilute hydrochloric acid.

The fluorogens of formula I wherein $R_1$ and $R_2$ are as above and $R_3$ is other than carboxy or carboxy lower alkyl substituted phenyl, naphthyl or indolyl are relatively insoluble in water and react slowly with water to afford decomposition products which are non-fluorescent. The fluorogens of formula I are readily soluble in organic solvents and are particularly soluble in solvents such as acetone and dichloromethane. Since the compounds have low water solubility, when it is desired to react them with materials which are present in aqueous media, either as a solution or as a suspension, it is preferable to add then either as a solution in an organic solvent such as acetone, or to carry out the reaction by having the compound of formula I adsorbed onto a solid support. This latter technique of adsorption onto a solid support is particularly preferred when reacting the fluorogen with materials which are soluble in the aqueous medium so that any unreacted fluorogen of formula I adsorbed on the solid support may be removed by filtration or centrifugation. Suitable solid supports include neutral inert material such as diatomaceous earth, polysaccharides, and so forth. A particularly preferred solid support is diatomaceous earth. Adsorption of the compound of formula I onto the solid suport may be performed by methods known per se, for example, by suspending the solid support in a solution containing the compound of formula I, for example, a solution in acetone or methylene chloride, and evaporating the solvent from said suspension followed by thorough air drying or drying under vacuum. It is most preferable to prepare solid supports containing from about 0.1 to about 5.0 weight % of compounds of formula I, most preferably from about 1 to 2 weight %.

Fluorogens of formula I react with primary amine containing materials to form flourescent products. The types of materials which may be reacted with the fluorogens of formula I include primary amines; amino acids; peptides; proteins, particularly those of biological significance such as immunoglobulins (antibodies); viruses; unicellular organisms such as bacteria, protozoa, algae and fungi; and multicellular organisms, for example, helminths, such as tapeworms. The effect of reacting a compound of formula I with one of the aforementioned materials is to introduce a fluorescent label into said material. The introduction of the fluorescent label allows for rapid identification of such material using fluorescent technology, particularly fluorescent microscopy. The use of fluorescent labeling is particularly important in the field of labeling proteins, particularly those of biological importance such as antibodies. A major advantage of the compounds of the present invention is that they themselves are non-fluorescent, but upon reaction with materials containing primary amino groups, produce fluorescent material. Further, upon reaction with water contained in the reaction medium, the compounds of formula I will decompose into materials which are also non-fluorescent. Thus, the purification and isolation of the fluorescently labeled material is greatly simplified, since it is not necessary to separate these materials from an unreacted fluorogenic reagents, or decomposition products thereof, as is the case with prior art labeling techniques such as FITC.

It has been found that the fluorescent labeling reaction utilizing compounds of formula I is greatly dependent upon pH. The labeling occurs at a substantial rate between pHs of about 8.0 and 10.5. An optimal pH range for effecting the labeling is between about pH 9.0 and about 9.5. pH may be controlled by techniques known per se for adjusting pH, including the use of buffers. However, the use of buffers containing free primary amino groups should be avoided.

It has also been found that the fluorescent labeling reaction utilizing compounds of formula I wherein $R_1$ and $R_2$ are as above and $R_3$ is carboxy or carboxy lower alkyl substituted phenyl, naphthyl or indolyl can be advantageously performed in aqueous media at pHs of between about 8.0 and 10.5, optimally at a pH range of between about 9.0 and 9.5, thereby obviating the need for co-solvents or solid supports when primary amino biological materials dissolved or suspended in aqueous media are to be labeled. The carboxy substituted fluorogens, like the alkali insoluble fluorogens of formula I wherein $R_1$ and $R_2$ are as above and $R_3$ is phenyl, naphthyl or indolyl; or phenyl, naphthyl or indolyl substituted by halogen, lower alkyl, trifluoromethyl, lower alkoxy, nitro or cyano, slowly decompose in aqueous media between pHs of about 8.0 to about 10.5 to non-fluorescent decomposition products, eliminating the need for isolation and purification procedures.

The extent of labeling a particular substrate will vary depending upon the concentration of fluorogen utilized and the total contact time between the fluorogen and the substrate.

The extent of labeling desired for any particular substrate and purpose will of course vary from case to case. It has been found that extensive labeling for most purposes, can be achieved with a contact time between about 2 mins. and 2 hrs., most preferably between about 5 mins. and 30 mins.

The fluorescent excitation and emission spectra for the labeled materials will also vary depending upon the nature of the material. As an example, there may be mentioned a typical fluorescent spectrum for a gamma-globulin fraction labeled with a compound of formula I in which there are two excitation maxima, at 290 and 390 nm, and an emission maximum at 480 nm.

It has further been found that labeling of living substrates such as bacteria or tapeworms with fluorogens of formula I can have little, if any, effect upon their viability. Thus, the present procedure provides an efficient method for labeling living organisms. It has also been found that labeling of biologically important proteins such as antibodies has little, if any, effect upon their biological properties. For example, if antibodies against pneumococcus Type II are fluorescently labeled in accordance with the above technique, the antibody titer remains largely unaffected and, more importantly, the specificity of the antibody remains unchanged. In this case, for example, the antibodies were still specific for pneumococcus Type II and would not bind with pneumococcus Type I.

One additional feature of the labeled materials prepared by the above technique is that they are unusually stable for long periods of time, even at room temperature and in the presence of light. Thus, there is little destruction of the fluorescent label introduced into a variety of substrates, including both living and nonliving substrates over periods as long as one month.

The present invention may be more fully understood and appreciated by reference to the following specific examples.

EXAMPLE 1

To a mechanically stirred mixture of 83.2 g benzalacetophenone (0.3m), 1000 ml methanol and 120 ml 15% hydrogen peroxide was added 100 ml 2N sodium hydroxide solution, while maintaining the temperature below 30° by external cooling. After completed addition, the mixture was left standing at room temperature for 20 min. The crystalline precipitate was filtered off, washed with water and recrystallized from methanol. There were obtained 59.6 g 1,3-diphenyl-2,3-epoxy-1-propanone; m.p. 90 °C.

Calc. for $C_{15}H_{12}O_2$ (MW 224): C, 80.33; H, 5.39. Found: C, 80.05; H, 5.35.

EXAMPLE 2

To a boiling solution of 30 g 1,3-diphenyl-2,3-epoxy-1-propanone in 500 ml methanol was rapidly added a hot solution of 30 g potassium t-butoxide in 500 ml ethanol. The mixture was kept boiling on a steambath for 2 minutes. It was then diluted with 3 l. water. The aqueous solution was saturated with carbon dioxide by the addition of small pieces of dry ice. The resulting emulsion was extracted with ether. The ether extracts were diluted with benzene, dried over sodium sulfate and evaporated under reduced pressure. The remaining dark oil was distilled in high vacuum to afford 19.5 g 1,3-diphenyl-1,2-propanedione; b.p. 136°–138° /0.1 mm.

Calc. for $C_{15}H_{12}O_2$ (MW 224): C, 80.33; H, 5.39. Found: C, 80.01; H, 5.38.

EXAMPLE 3

A solution of 44.8 g 1,3-diphenyl-1,2-propanedione in 90 ml N,N-dimethylformamide dimethyl acetal was allowed to stand at room temperature for 2 hours. It was then poured into 1 l. ice/water. The aqueous mixture was extracted three times with ether. The combined extracts were washed with water, diluted with benzene, dried over sodium sulfate and evaporated under reduced pressure. The oily residue was crystallized from ether/petroleum ether to give 40.2 g of the desired product. A second crop of 3.1 g was obtained from the mother liquor upon concentration and addition of petroleum ether.

Total Yield: 43.3 g 1-dimethylamino-2,4-diphenyl-1-butene-3,4-dione; m.p. 108° C.

Calc for $C_{18}H_{17}NO_2$ (MW 279): C, 77.39; H, 6.13; N, 5.01. Found: C, 77.38; H, 6.10; N, 4.91.

EXAMPLE 4

To a solution of 43.3 g 1-dimethylamino-2,4-diphenyl-1-butene-3,4-dione in 500 ml ethanol was added 500 ml 2% aqueous potassium hydroxide. The mixture was stirred at room temperature for 2 hours. It was then diluted with 3 l. water and acidified with 10% hydrochloric acid. The solid 2-hydroxy-2,4-diphenyl-3(2H)-furanone, which precipitated, was filtered off with suction. The filter-cake was washed with water, and dissolved (without further purification) in 500 ml methanol. The methanolic solution was refluxed for 20 hrs., then concentrated on the steambath to approximately 350 ml. Crystalline product was obtained upon refrigeration. This was further purified by recrystallizing twice from methanol, yielding 25.5 g of the desired material; m.p. 93°–95° C. The mother liquors were combined and evaporated. The residue was redissolved in chloroform and filtered through 200 g silica gel. The eluate was evaporated and the residue was recrystallized from ethanol, giving an additional 5.8 g product; m.p. 93°–95°.

Total Yield: 31.3 g 2-methoxy-2,4-diphenyl-3(2H)-furanone, m.p. 93°–95° C.

Calc. for $C_{17}H_{14}O_3$ (MW 266): C, 76.67; H, 5.30. Found: C, 76.65; H, 5.48.

EXAMPLE 5

Following the procedures of examples 1-4, the following compounds, including the respective intermediates in their preparation, were prepared:

2-ethoxy-2,4-diphenyl-3(2H)-furanone, m.p. 87°: Calc. for $C_{18}H_{16}O_3$ (MW 280): C, 77.12; H, 5.75. Found: C, 77.39; H, 5.92.

2-Benzyloxy-2,4-diphenyl-3(2H)-furanone, m.p. 140°: Calc. for $C_{23}H_{18}O_3$ (MW 342): C, 80.68; H, 5.30. Found: C, 80.57; H, 5.28.

2-methoxy-2-phenyl-4-(4-nitrophenyl)-3(2H)-furanone, m.p. 115°–117°.

EXAMPLE 6

Following the procedure of examples 1-4, there may be prepared the following compounds:

2-methoxy-2-phenyl-4-(2-naphthyl)-3(2H)-furanone;

2-methoxy-2-(4-chlorophenyl)-4-phenyl-3(2H)-furanone;

2-ethoxy-2-(2,4-dimethoxyphenyl)-4-(3-indolyl)-3(2H)-furanone;

2-methoxy-2-phenyl-4-(2-trifluoromethylphenyl)-3(2H)-furanone.

EXAMPLE 7

A solution of 43 g of terephthaldehyde and 33.5 g of malonic acid in 100 ml of pyridine and 100 ml of ethanol was heated at 90°–95° for 16 hrs. with stirring and then allowed to stand at room temperature for 4 days. The reaction mixture was cooled in an ice-bath, 200 ml of 1N hydrochloric acid was added and after stirring for about 1/2 hr., the precipitate was collected, washed with water, 100 ml of 1N hydrochloric acid, water and dried at 70°–75° under vacuum for 24 hrs.; yield 37 g (49%) of 4-formylcinnamic acid.

A solution of 37.0 g of 4-formylcinnamic acid in 22 ml of trimethyl orthoformate and 600 ml of methanol was heated under reflux for 17 hrs. with stirring. At the end of this time, 100 ml of methanol was added and the reaction mixture was heated under reflux for an additional 5 hrs. and then allowed to cool to room temperature. The precipitate was collected, washed with methanol and dried at 75°–80° overnight to give 7.36 g of 4-carboxycinnamic acid.

The methanolic filtrate was evaporated to dryness. The residue was dissolved in 1 l. of methylene chloride and the solution was filtered through Celite. The filtrate was concentrated to a volume of 250 ml and stored at 0° for 16 hours. The precipitate was collected, washed with methylene chloridepetroleum ether (1:1) and dried at 60° under vacuum for 3 hrs. to give 31.2 g (43.7%) of 4-formylcinnamic acid dimethyl acetal as colorless crystals, m.p. 131°–133°.

A solution of 16.7 g of 4-formylcinnamic acid dimethyl acetal in 200 ml of dioxane was hydrogenated in the presence of 1 g of 5% palladium-on-carbon at room temperature and atmospheric pressure. After about 6½ hrs., the theoretical volume of hydrogen was consumed and the uptake ceased. The reaction mixture was filtered through Celite and the filter cake was washed with 300 ml of dioxane. The filtrate was concentrated to a final volume of 200 ml, 200 ml of 1N hydrochloric acid was added, the solution was stirred at room temperature for 4 hrs. and then evaporated to dryness. The residue was dissolved in 700 ml of methylene chloride, dried over anhydrous sodium sulfate and filtered. The filtrate was concentrated to a final volume of 100 ml and the solution was allowed to stand at 0° for 16 hrs. The precipitate was collected, washed with 1:1 methylene chloride-petroleum ether and dried at 55° for 4 hrs. under vacuum to give 10.9 g (81%) of 4-formyldihydrocinnamic acid as colorless crystals, m.p. 134°–138°.

To a solution of 5.34 g of 4-formyldihydrocinnamic acid in 50 ml of 1N sodium hydroxide was added a solution of 3.6 g of acetophenone and 20 ml of ethanol. The reaction mixture was stirred at room temperature for 4 hrs. and then poured onto 300 g of crushed ice. 1N Hydrochloric acid was added and, after stirring at 0°C for 15 min., the precipitate was collected and washed with water. The precipitate was dissolved in 500 ml of ethyl acetate, dried over anhydrous sodium sulfate and the drying agent was collected on a filter. The filtrate was concentrated to about 100 ml and seeded with crystalline product. The solid was collected, washed with 1:4-ethyl acetate-ether followed by ether and dried at 70°–75°C under vacuum to give 8.4 g (72%) of 4-(2-carboxyethyl)benzalacetophenone, as yellow needles, m.p. 159°–160°C.

EXAMPLE 8

To a suspension of 5.6 g of 4-(2-carboxyethyl)benzalacetophenone and 20 ml of 1N sodium hydroxide solution was added 4 ml of 30% hydrogen peroxide at room temperature. The mixture was cooled in an ice-bath and 15 ml of 0.5N sodium hydroxide solution was added dropwise over a few min. with stirring. The reaction mixture was stirred at room temperature for 3 hrs. and then the pH was adjusted from 9.4 to 4.5 by the addition of 1N hydrochloric acid. After about ½ hr., the precipitate was collected. The precipitate was dissolved in 200 ml of ethyl acetate, dried over anhydrous sodium sulfate and filtered. The filtrate was evaporated. The residue was dissolved in 100 ml of boiling ethyl acetate. About 50 ml of the solvent was evaporated and 50 ml of ether was added. The solution was concentrated to about 25 ml and after standing at room temperature for 17 hrs., the solid was collected, washed with 1:4-ethyl acetate-ether followed by ether and dried under vacuum at 60°–65°C to give 3.3 g (55%) of 3-[4-(2-carboxyethyl)phenyl]-1-phenyl-2,3-epoxy-1-propanone as colorless crystals.

EXAMPLE 9

To a solution of 2.96 g of 3-[4-(2-carboxyethyl)-phenyl]-1-phenyl-2,3-epoxy-1-propanone in 50 ml of ethanol at 85°–90°C was added a solution of 2.9 g of potassium hydroxide in 50 ml of ethanol also at 85°–90°C over a 3 min. period. The reaction mixture was stirred at 85°–90°C for 5 min. and then cooled to room temperature. The reaction mixture containing a small amount of solid impurity was filtered and the filtrate was evaporated. The residue was dissolved in 200 ml of ice-water and acidified with 75 ml of 1N hydrochloric acid. The mixture was extracted with methylene chloride, the layers were separated and the combined organic phase was washed with water. The organic phase was dried, filtered and the filtrate was evaporated to dryness at 20°–35°C under high vacuum to give 3.0 g of a yellow solid.

Recrystallization of the solid from ether-petroleum ether gave 1.98 g (67%) of 3-[4-(2-carboxyethyl)-phenyl]-1-phenyl-1,2-propanedione as yellow crystals after drying at 55°–60°C for 3 hrs. under vacuum.

EXAMPLE 10

To a solution of 4.44 g of 3-[4-(2-carboxyethyl)-phenyl]-1-phenyl-1,2-propanedione in 25 ml of dry dimethylformamide, cooled in an ice-bath, was added 11 ml of dimethylformamide dimethyl acetal. After stirring at room temperature for 15 min., the reaction mixture was poured onto 300 ml of crushed ice and the reaction mixture was acidified with 25 ml of 1N hydrochloric acid. The mixture was extracted with methylene chloride. The layers were separated and the organic phase was washed with water, dried, filtered and evaporated under vacuum. Recrystallization of the residue from methylene chloride-ether gave 3.95 g (75%) of 2-[4-(2-carboxyethyl)phenyl]-1-dimethylamino-4-phenyl-1-butene-3,4-dione as yellow crystals after drying at 50°C for 3 hrs.

EXAMPLE 11

A solution of 3.95 g of 2-[4-(2-carboxyethyl)-phenyl]-1-dimethylamino-4-phenyl-1-butene-3,4-dione in 100 ml of 2% potassium hydroxide solution was stirred at room temperature for 3½ hrs. The reaction mixture was poured onto 300 ml of ice-water, acidified with 100 ml of 1N hydrochloric acid and extracted with methylene chloride. The organic extract was washed with water, dried, filtered and evaporated. Recrystallization of a sample of the residue from methylene chloride-petroleum ether gave 2-hydroxy-2-phenyl-4-[4-(2-carboxyethyl)phenyl]-3(2H)-furanone as colorless crystals, m.p. 89°–95° dec., after drying at 50°C.

Yield: 93%.

EXAMPLE 12

A solution of 3.36 g of 2-hydroxy-2-phenyl-4-[4-(2-carboxyethyl)phenyl]-3(2H)-furanone in 150 ml of methanol was heated under reflux under a nitrogen atmosphere for 17 hrs. The reaction mixture was evaporated and the residue was recrystallized from methylene chloride-petroleum ether to give 2.28 g (83%) of 2-methoxy-2-phenyl-4-[4-(2-carboxyethyl)phenyl]-3-(2H)-furanone as colorless crystals, m.p. 117°–120°C, after drying at 50°C for 1 hr. under vacuum.

EXAMPLE 13

To a solution of 2.0 g of sodium hydroxide in 25 ml of water and 10 ml of ethanol was added 4.50 g of 4-carboxybenzaldehyde (supplied by the Aldrich Chemical Company, Milwaukee, Wis.) in one portion. After stirring for 15 min. at room temperature, 3.60 g of acetophenone was added and the resulting solution was stirred at room temperature for 3 hrs. The reaction mixture was cooled in an ice-bath and acidified with 75 ml of 1N hydrochloric acid. The precipitate was collected, washed with water and air-dried. Recrystallizaton from methanol gave 4.64 g (61%) of 4-carboxybenzalacetophenone as yellow crystals, m.p. 227°–229°C after drying at 90°–95°C under vacuum for 4 hrs.

Calc. for $C_{16}H_{12}O_3$ (MW 252): C, 76.18; H, 4.80. Found: C, 76.29; H, 4.81.

EXAMPLE 14

To a solution of 18.9 g of 4-carboxybenzalacetophenone in 7.5 ml of 1N sodium hydroxide solution and 225 ml of water was added 15 ml of 30% hydrogen peroxide. After cooling in an ice-water bath, 50 ml of 0.5N sodium hydroxide was added dropwise over 5 min. The reaction mixture was stirred at room temperature for 3¼ hrs. and acidified to pH of 6.5 with 1N hydrochloric acid. After stirring at room temperature for 1 hr., the solid was collected on a filter, washed with water and air-dried. Recrystallization from ethanol gave 11 g of 3-(4-carboxyphenyl)-1-phenyl-2,3-epoxy-1-propanone as colorless crystals, m.p. 170°–172°C after drying at 80°C under vacuum for 3 hrs.

The pH of the filtrate of the first filtration was adjusted to 5.0 with 1N hydrochloric acid. The solid was collected and recrystallized from the mother liquor of the first recrystallization to give 4.9 g of the product as colorless crystals, m.p. 170°–172°C.

Total yield 15.9 g (79%).

Calc. for $C_{16}H_{12}O_4$ (MW 268): C, 71.63; H, 4.51. Found: C, 71.64; H, 4.47.

EXAMPLE 15

To a solution of 5.63 g of 3-(4-carboxyphenyl)-1-phenyl-2,3-epoxy-1-propanone in 100 ml of ethanol at 85°–90°C was added a solution of 6 g of potassium hydroxide in 100 ml of ethanol with stirring over 5 min. The reaction mixture was heated at 85°–90°C for 5 min. and then allowed to cool to room temperature. The solution was evaporated to dryness and the residue was dissolved in 300 ml of ice-water and acidified with 125 ml of hydrochloric acid. After stirring for 30 min., the precipitate was collected and washed with water. The precipitate was dissolved in 600 ml of ethyl acetate and the solution was dried and filtered. The filtrate was evaporated to give 5.63 g (100%) of 3-(4-carboxyphenyl)-1-phenyl-1,2-propanedione as a yellow solid.

An analytical sample prepared by recrystallization from ethyl acetate had m.p. 192°–195°C.

Calc. for $C_{16}H_{12}O_4$ (MW 268): C, 71.63; H, 4.51. Found: C, 71.54; H, 4.44.

EXAMPLE 16

To a solution of 3-(4-carboxyphenyl)-1-phenyl-1,2-propanedione in 100 ml of dry dimethylformamide cooled in an ice-bath was added, with stirring, 56 ml of dimethylformamide dimethyl acetal. The reaction mixture was stirred at 0°–5°C for 10 min. and then it was poured onto 1.2 l of ice-water and acidified with 130 ml of 1N hydrochloric acid. After stirring for 5 min., 1.8 l of water was added and the precipitate was collected, washed with water and air-dried. The filter cake was dissolved in 1.7 l of methylene chloride, dried over anhydrous sodium sulfate, filtered and the filtrate was concentrated to about 200 ml. Ether (200 ml) was added and the solution was concentrated to about 300 ml and allowed to stand at room temperature for 2 days. The solid was collected, washed with methylene chloride-ether (1:9) and dried at 80°C for 3 hrs. to give 17.4 g (44%) of 2-(4carboxyphenyl)-1-dimethylamino-4-phenyl-1-butene-3,4-dione as yellow crystals, m.p. 208°–209°C.

Calc. for $C_{19}H_{17}NO_4$ (MW 323): C, 70.57; H, 5.30; N, 4.33. Found: C, 70.32; H, 5.31; N, 4.33.

EXAMPLE 17

A solution of 3.23 g of 2-(4-carboxyphenyl)-1-dimethylamino-4-phenyl-1-butene-3,4-dione in 100 ml of 2% potassium hydroxide solution was stirred at room temperature for 5 hrs. The reaction mixture was poured onto 300 ml of ice-water and acidified with 100 ml of 1N hydrochloric acid. The precipitate was collected, washed with water and then dissolved in 300 ml of ether. The solution was dried over anhydrous sodium sulfate. The drying agent was collected and the filtrate was evaporated. Recrystallization from ether gave 2.12 g (71%) of 2-hydroxy-2-phenyl-4-(4-carboxyphenyl)-3(2H)-furanone, m.p. 294°–299°C. dec.

Calc. for $C_{17}H_{12}O_5$ (MW 296): C, 68.91; H, 4.08. Found: C, 68.89; H, 3.98.

EXAMPLE 18

A solution of 1.50 g of 2-hydroxy-2-phenyl-4-(4-carboxyphenyl)-3(2H)-furanone in 100 ml of methanol was heated under reflux with stirring for 17 hrs. The reaction mixture was concentrated to a volume of 20 ml, seeded with the product and the precipitate was collected after standing at 0°C for 3 days. The precipitate was collected, washed with cold methanol and ether and dried at 0°C for 4 hrs. to give 1.42 g (91.6%) of 2-methoxy-2-phenyl-4-(4-carboxyphenyl)-3(2H)-furanone as colorless crystals, m.p. 212°–214°C.

Calc. for $C_{18}H_{14}O_5$ (MW 310): C, 69.67; H, 4.55. Found: C, 69.47; H, 4.56.

EXAMPLE 19

Mouse tapeworms (Hymenolepis nana) in 9 ml of aqueous buffer, pH 9.5, were stained for 10 minutes at 22°–26°C by adding 1 ml of an acetone solution (of various concentrations) of 2-methoxy-2,4-diphenyl-3(2 H)-furanone. Excess dye was removed by washing the worms in BME (eagles basal medium) culture medium. The intensity of fluorescence, judged on an arbitrary scale from no staining (0) to maximum staining (1.00), was determined using an American Optical Fluorescent microscope at 1 hr., 22 hr. and 8 days after staining. These results are presented below. Both gross morphology and activity of the worms appeared to be unaffected by the staining procedure.

| Concentration mg/ml | Time post staining | | |
|---|---|---|---|
| | 1 Hr. | 22 hrs. | 8 days |
| 0.0 | 0.06 | 0.06 | 0.06 |
| 0.5 | 0.37 | 0.37 | 0.50 |
| 0.1 | 0.67 | 0.67 | — |
| 0.2 | 0.75 | 0.75 | 0.67 |

EXAMPLE 20

Escherichia coli was suspended in 9 ml borate buffered saline solution, pH 9.5, and was stained for 30–60 mins. at room temperature by adding 1 ml of an acetone solution (of various concentrations) of 2-methoxy-2,4-diphenyl-3(2 H)-furanone. Excess dye was removed by centrifugation, the bacteria were resuspended in saline, stored at 4°C and samples were examined for fluorescence at 24 hr., 8 days and 16 days post staining. Cell viability was estimated at 22 hrs. post staining by a standard plate count technique. Staining intensity was judged on an arbitrary scale from no staining (0) to maximum staining (1.00). The results are presented below:

| Conc. mg/ml | Time post staining | | | Cell viability |
|---|---|---|---|---|
| | 1 day | 8 days | 16 days | |
| 0.0 | 0.00 | 0.00 | 0.00 | $2 \times 10^8$ |
| 0.05 | 0.67 | 0.67 | 0.67 | — |
| 0.1 | 1.00 | 0.87 | 0.87 | $7 \times 10^6$ |
| 0.2 | 1.00 | 1.00 | 0.87 | $4.5 \times 10^5$ |

EXAMPLE 21

Specific Type II rabbit antipneumococcal serum was diluted in buffer, pH 9.0, and reacted for 10 minutes at room temperature with celite (diatomaceous earth) containing 1% or 2% w/w of 2-methoxy-2,4-diphenyl-3(2 H)-furanone. The celite was then removed by filtration or centrifugation and the labeled serum stored at 4°C. Saline suspension of Type II pneumococci were placed on microscope slides. The bacteria, after air drying, were fixed to the slides by heat, and stained with labeled Type II antiserum for 10–30 mins. at room temperature. Excess antiserum was removed by washing the slides with saline and fluorescence was determined under direct oil immersion. Staining intensity was measured at 10, 25 and 31 days post labeling, and was judged on an arbitrary scale from no staining (0) to maximum staining (1.00). The results are presented below:

| Time post labeling (days) | Dilution of labeled serum | |
|---|---|---|
| | 1:10 | 1:100 |
| | Staining Intensity | |
| 0 | 0.87 | — |
| 10 | 0.75 | 1.00 |
| 25 | 0.75 | — |
| 31 | 0.87 | 1.00 |

No fluorescence was seen when Type I pneumococci were used as antigen, thus indicating that immunological specificity was retained.

The effect of labeling on antibody titer was determined by standard Immunological tests. The results are presented below. The titer is expressed as the reciprocal of the last serum dilution giving a positive reaction.

| Immunologic Test | Titer | |
|---|---|---|
| | labeled/serum | unlabeled/serum |
| Quellung Reaction | 100 | 80 |
| Latex slide agglutination | 400 | 320–640 |
| Fluorescent microscope: | | |
| 14 days post labeling | 640–1280 | 0 |
| 31 days post labeling | 400–800 | 0 |

EXAMPLE 22

50 mg of γ-globulin (horse, >98% pure) was dissolved in 500 ml of 0.05 M buffers of varying pH. 200 mg celite containing 2% w/w of 2-methoxy-2,4-diphenyl-3(2 H)-furanone (prepared by treating 10 g celite with a solution of 200 mg of the furanone in acetone and evaporating to dryness) was added. After 15 mins. of stirring magnetically at room temperature, the mixture was filtered through a fine funnel, the filtrate was frozen in dry ice-acetone and stored in a freezer. Fluorescence was measured after centrifugation. Relative fluorescence is given in arbitrary units.

| pH | rel. fluorescence |
|---|---|
| 8.00 | 4 |
| 8.35 | 9.5 |
| 8.50 | 16 |
| 8.83 | 33 |
| 9.00 | 46 |
| 9.31 | 75 |
| 9.50 | 80.5 |
| 9.75 | 84 |
| 10.06 | 89 |

Identical results were obtained after allowing the solutions to stand for 3 days at room temperature.

EXAMPLE 23

20 ml of 1% solutions of γ-globulin (horse,>98%) in buffer, either pH 9.00 or 9.50, were labeled by treatment with 200 mg of celite containing 2% w/w of 2-methoxy-2,4-diphenyl-3(2H)-furanone at room temperature for 10 mins. The solutions were neutralized immediately to pH 7.00 with 1 N HCl, centrifuged, and the supernatant was stored at room temperature. Relative fluorescence was measured (activation 390 nm, emission 484 nm) at various intervals, and is given in arbitrary units.

| pH 9.00 | |
|---|---|
| Days post labeling | Rel. fluorescence |
| 0 | 56.0 |
| 1 | 56.0 |
| 2 | 55.5 |
| 4 | 56.0 |
| 6 | 57.0 |
| 8 | — |
| 11 | 55.0 |

| pH 9.50 | |
|---|---|
| Days post labeling | Rel. Fluorescence |
| 0 | 89.5 |
| 1 | 89.0 |
| 2 | 88.0 |
| 4 | 88.0 |
| 6 | 89.0 |
| 8 | — |
| 11 | 86.0 |

EXAMPLE 24

Human washed platelets were labeled by exposure to a saline solution containing 5 mg/ml of 2-methoxy-2-phenyl-4-(4-carboxyphenyl)-3(2H)-furanone following essentially the hereinbefore described labeling procedures. Excess reagent was washed from the platelets and fluorescence was detected under a fluorescent microscope. The platelets were fluorescent.

We claim:
1. A compound of the formula

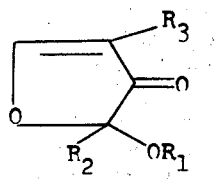

wherein $R_1$ is lower alkyl or phenyl lower-alkyl, $R_2$ is phenyl, lower-alkoxyphenyl, di-lower-alkoxyphenyl, carboxyphenyl or carboxy-lower-alkylphenyl and $R_3$ is phenyl or nitrophenyl.

2. A compound according to claim 1 wherein $R_1$ is lower alkyl.

3. A compound according to claim 1 wherein $R_2$ and $R_3$ are both phenyl.

4. The compound of claim 3 which is 2-methoxy-2,4-diphenyl-3(2H)-furanone.

5. The compound of claim 3 which is 2-ethoxy-2,4-diphenyl-3(2H)-furanone.

6. The compound of claim 3 which is 2-benzyloxy-2,4-diphenyl-3(2H)-furanone.

7. The compound of claim 2 which is 2-methoxy-2-phenyl-4(4-nitrophenyl)-3(2H)-furanone.

8. The compound of claim 2 which is 2-methoxy-2-phenyl-4-(4-carboxyphenyl)-3(2H)-furanone.

9. The compound of claim 2 which is 2-methoxy-2-phenyl-4-[4-(2-carboxyethyl)phenyl]-3(2H)-furanone.

* * * * *

UNITED STATES PATENT AND TRADEMARK OFFICE
CERTIFICATE OF CORRECTION

PATENT NO. : 3,969,373
DATED : July 13, 1976
INVENTOR(S) : Roy Cleeland, Jr., Emanuel Grunberg, Willy Leimgruber and Manfred Weigele It is certified that error appears in the above-identified patent and that said Letters Patent are hereby corrected as shown below:

Column 16, lines 3 and 4, "carboxyphenyl or carboxy-lower-alkylphenyl and $R_3$ is phenyl or nitrophenyl." should be ---- and $R_3$ is carboxyphenyl, carboxy-lower-alkylphenyl, phenyl or nitrophenyl. ----.

Signed and Sealed this

Eleventh Day of October 1977

[SEAL]

Attest:

RUTH C. MASON
Attesting Officer

LUTRELLE F. PARKER
Acting Commissioner of Patents and Trademarks